US010865255B2

(12) United States Patent
Andreasen

(10) Patent No.: US 10,865,255 B2
(45) Date of Patent: *Dec. 15, 2020

(54) STABLE IRON OLIGOSACCHARIDE COMPOUND

(71) Applicant: Pharmacosmos Holding A/S, Holbæk (DK)

(72) Inventor: Hans Andreasen, Holbaek (DK)

(73) Assignee: Pharmacosmos Holding A/S, Holbaek (DK)

( * ) Notice: Subject to any disclaimer, the term of this patent is extended or adjusted under 35 U.S.C. 154(b) by 20 days.

This patent is subject to a terminal disclaimer.

(21) Appl. No.: 15/222,306

(22) Filed: Jul. 28, 2016

(65) Prior Publication Data

US 2016/0333118 A1  Nov. 17, 2016

Related U.S. Application Data

(62) Division of application No. 14/307,957, filed on Jun. 18, 2014, now Pat. No. 9,439,969, which is a division of application No. 13/138,669, filed as application No. PCT/DK2009/050069 on Mar. 25, 2009, now Pat. No. 8,815,301.

(51) Int. Cl.
| | | |
|---|---|---|
| *C08B 37/02* | (2006.01) | |
| *C07H 3/06* | (2006.01) | |
| *A61K 31/721* | (2006.01) | |
| *A61K 47/26* | (2006.01) | |

(52) U.S. Cl.
CPC ........ *C08B 37/0021* (2013.01); *A61K 31/721* (2013.01); *A61K 47/26* (2013.01); *C07H 3/06* (2013.01)

(58) Field of Classification Search
CPC ............ C07H 3/06; C07H 37/00–0024; A61K 31/702; A61K 31/715–721
See application file for complete search history.

(56) References Cited

U.S. PATENT DOCUMENTS

| | | | |
|---|---|---|---|
| 2,807,610 | A | 9/1957 | Zief et al. |
| 3,076,798 | A | 2/1963 | Mueller et al. |
| 3,100,202 | A | 8/1963 | Muller et al. |
| 3,639,588 | A | 2/1972 | Alsop et al. |
| 4,201,772 | A | 5/1980 | Ingelman et al. |
| 4,518,581 | A | 5/1985 | Miyake et al. |
| 4,599,405 | A | 7/1986 | Muller et al. |
| 4,749,695 | A | 6/1988 | Schwengers |
| 4,927,756 | A | 5/1990 | Schwengers |
| 5,624,668 | A | 4/1997 | Lawrence et al. |
| 6,291,440 | B1 | 9/2001 | Andreasen et al. |
| 6,599,498 | B1 | 7/2003 | Groman et al. |
| 6,960,571 | B2 | 11/2005 | Helenek et al. |
| 6,977,249 | B1 | 12/2005 | Andreasen et al. |
| 7,612,109 | B2 | 11/2009 | Geisser et al. |
| 7,754,702 | B2 | 7/2010 | Helenek et al. |
| 7,871,597 | B2 | 1/2011 | Groman et al. |
| 8,431,549 | B2 | 4/2013 | Helenek et al. |
| 8,815,301 | B2 | 8/2014 | Andreasen |
| 8,895,612 | B2 | 11/2014 | Helenek et al. |
| 9,439,969 | B2 | 9/2016 | Andreasen |
| 10,414,831 | B2 | 9/2019 | Andreasen |
| 2003/0083310 | A1 | 5/2003 | Andreasen et al. |
| 2003/0191090 | A1 | 10/2003 | Andreasen et al. |
| 2003/0232084 | A1 | 12/2003 | Groman et al. |
| 2004/0180849 | A1 | 9/2004 | Helenek et al. |
| 2006/0116349 | A1 | 6/2006 | Helenek et al. |
| 2006/0205691 | A1 | 9/2006 | Geisser et al. |
| 2007/0161600 | A1 | 7/2007 | Helenek et al. |
| 2008/0214496 | A1 | 9/2008 | Tanner-Baumgartner et al. |
| 2008/0234226 | A1 | 9/2008 | Erichsen et al. |
| 2010/0266644 | A1 | 10/2010 | Helenek et al. |
| 2010/0305063 | A1 | 12/2010 | Reim et al. |
| 2013/0230565 | A1 | 9/2013 | Helenek et al. |
| 2014/0099381 | A1 | 4/2014 | Helenek et al. |
| 2014/0121193 | A1 | 5/2014 | Katz et al. |
| 2014/0364598 | A1 | 12/2014 | Andreasen |
| 2015/0320031 | A1 | 11/2015 | Andreasen et al. |
| 2016/0333118 | A1 | 11/2016 | Andreasen |

FOREIGN PATENT DOCUMENTS

| | | |
|---|---|---|
| AU | 740432 | 10/1999 |
| AU | 2009342799 | 12/2014 |
| CA | 623411 A | 7/1961 |

(Continued)

OTHER PUBLICATIONS

Paul, F, et al "Acceptor reaction of a highly purified dextransucrase . . . " Carbohyd. Res., vol. 149, pp. 433-441 (Year: 1986).*
International Search Report dated Oct. 12, 2009.
Dextran 1 entry European Pharmacopoeia (2004) 5th Edition, published by Council of Europe, Strasbourg, pp. 1408-1409.
Final Office Action dated Apr. 27, 2017 for U.S. Appl. No. 14/308,198.
"Publication Under Section 43(2) in Respect of the Grant, "extract from the official journal of the patent office dated Dec. 29, 2017. 2 pages.
Certified as-filed granted Indian Patent No. 291100 dated Dec. 13, 2018. 26 pages.
Examination Report received in Indian Patent No. 291100 (Appl. No. 8145/DELNP/2011) dated Jun. 16, 2017 and Response to Examination Report dated Dec. 15, 2017. 33 pages.

(Continued)

*Primary Examiner* — Leigh C Maier
(74) *Attorney, Agent, or Firm* — Robin L. Teskin; Baker, Donelson, Bearman, Caldwell & Berkowitz PC

(57) ABSTRACT

The invention relates to an iron oligosaccharide compound with improved stability comprising a hydrogenated oligosaccharide in stable association with ferric oxyhydroxide, the content of dimer saccharide in said hydrogenated oligosaccharide being 2.9% by weight or less, based on the total weight of the hydrogenated oligosaccharide. In further aspects is provided a process for preparing said compound as well as the use of said compound for preparation of a composition for treatment of iron deficiency anaemia.

28 Claims, 1 Drawing Sheet

(56) References Cited

FOREIGN PATENT DOCUMENTS

| CA | 623412 A | 7/1961 |
|---|---|---|
| CA | 2493806 A1 | 5/2004 |
| CA | 2617510 A1 | 3/2007 |
| CA | 2682587 A1 | 12/2008 |
| CN | 101365458 | 2/2009 |
| EA | 003427 | 2/2001 |
| GB | 1076219 A | 7/1967 |
| KR | 10-2005-0070014 | 7/2005 |
| KR | 10-2017-7005732 | 3/2017 |
| WO | WO-9711711 A1 | 4/1997 |
| WO | WO-9948533 A1 | 9/1999 |
| WO | WO 00/30657 | 6/2000 |
| WO | WO-0030657 A1 | 6/2000 |
| WO | WO-03087164 A1 | 10/2003 |
| WO | WO-2004037865 A1 | 5/2004 |
| WO | WO-2006084782 A1 | 8/2006 |
| WO | WO-2006111802 A1 | 10/2006 |
| WO | WO-07023154 A2 | 3/2007 |
| WO | WO 2007/081744 | 7/2007 |
| WO | WO-2008145586 A1 | 12/2008 |
| WO | WO 2014/058516 | 4/2014 |

OTHER PUBLICATIONS

Granted specification, including claims of Indian Patent No. 224635 issued Oct. 30, 2008.
Form 27 dated Mar. 9, 2018 in respect of Indian Patent No. 224635 issued Oct. 30, 2008. 2 pages.
Public Assessment Report (Scientific Discussion) concerning Monofer 100 mg/ml solution for injection/infusion dated Nov. 26, 2009. 11 pages.
EU Clinical Trials Register in respect of Monofer from search dated Jul. 24, 2018 from https://clinicaltrialsregister.eu. 2 pages.
Form 27 dated Jan. 17, 2018 in respect of corresponding Indian Patent No. 291100. 1 page.
Hedin H, et al. "Prevention of dextran anaphylaxis. Ten years experience with hapten dextran," Int Arch Allergy Immunol. May-Jul. 1997;113(1-3):358-9. 2 pages.
Preliminary opinion of the opposition division and response letter dated Sep. 8, 2003 by the applicant of EP 1066056, corresponding to Indian Patent No. 224635. 14 pages.
Jahn MR, et al. "A comparative study of the physicochemical properties of iron isomaltoside 1000 (Monofer), a new intravenous iron preparation and its clinical implications," Eur J Pharm Biopharm. Aug. 2011;78(3):480-91. 12 pages.
Goetsch, et al. "Observations on the effect of massive doses of iron given intravenously to patients with hypochromic anemia," Blood. Mar. 1946;1:129-42. 15 pages.
Nissim, JA. "Intravenous administration of iron," Lancet. Jul. 12, 1947;2(6463):49-51. 3 pages.
Nagy L, et al. "Equilibrium and structural studies on metal complexes of carbohydrates and their derivatives," J Inorg Biochem. Apr. 10, 2002;89(1-2):1-12. 12 pages.
Gyurcsik, B et al. "Carbohydrates as ligands: coordination equilibria and structure of the metal complexes," Coord Chem Rev, Jun. 2000; 203:81-149. 69 pages.
"Compound Summary for CID 439193; Isomaltose," Dec. 13, 2018 printout from the website https://pubchem.ncbi.nlm.nih.gov/compound/isomaltose#.section=Top 1 page.
Notarized Affidavit of Dr. Bipin Pandey filed with Written Statement of Opposition under Section 25(2) by the Opponent filed in corresponding Indian Patent No. 291100 filed Dec. 28, 2018, including annexure 1, CV of Dr. Bipin Pandey. 29 pages.
Written Statement of Opposition under Section 25(2) by the Opponent filed in corresponding Indian Patent No. 291100 filed Dec. 28, 2018. 49 pages.
Agarwal et al., "Oxidative stress and renal injury with intravenous iron in patients with chronic kidney disease." Kidney Int. Jun. 2004;65(6):2279-89.

Ahsan et al., "Efficacy of Bolus Intravenous Iron Dextran Treatment in Peritoneal Dialysis Patients Receiving Recombinant Human Erythropoietin" Adv Petit Dial. 1996;12:161-6.
Ali O., "Commissioning cost-effective delivery of intravenous iron." Prescriber. Oct. 2011;22(19):43-6.
Alvares et al., "Evaluation of cardiac function in iron deficiency anemia before and after total dose iron therapy" J Assoc Physicians India. Feb. 2000;48(2):204-6.
American Regent Press Release, American Regent Announces Enrollment of First Patient in Phase 3 Trial to Investigate Injectafer® (Ferric Carboxymaltose) as Treatment for Heart Failure with Iron Deficiency, Published Apr. 24, 2017.
Andersson, "Clinical Investigations on a new Intramuscular Haematinic." Br Med J. Jul. 1961;29;2(5247):275-9.
Arond et al., Molecular weight distribution and molecular size of a native dextran. The Journal of Physical Chemistry. Nov. 1954:58(11):953-7.
Aronoff, G.R., "Safety of intravenous iron in clinical practice: implications for anemia management protocols." J Am Soc Nephrol. Dec. 2004;15 Suppl 2:S99-106.
Auerbach et al., "Intravenous Iron Optimizes the Response to Recombinant Human Erythropoietin in Cancer Patients with Chemotherapy-Related Anemia: A Multicenter, Open-Label, Randomized Trial." J Clin Oncol. Apr. 1, 2004;22(7):1301-7.
Auerbach et al., "Low-molecular weight iron dextran and iron sucrose have similar comparative safety profiles in chronic kidney disease." Kidney Int. Mar. 2008;73(5):528-30.
Auerbach et al., "Safety and efficacy of total dose infusion of 1,020 mg of ferumoxytol administered over 15 min" Am J Hematol. Nov. 2013;88(11):944-7.
Auerbach et al., "Clinical Use of Intravenous Iron: Administration, Efficacy, and Safety." Hematology Am Soc Hematol Educ Program. 2010:338-47.
Bailie et al., "Hypersensitivity reactions and deaths associated with intravenous iron preparations." Nephrol Dial Transplant. Jul. 2005;20(7):1443-9.
Bailie, G. R., "Breaking New Ground in Intravenous Iron Therapy, European Haematology." 2008: 58-60.
Bailie, G. R., "Efficacy and safety of ferric carboxymaltose in correcting iron-deficiency anemia: a review of randomized controlled trials across different indications." Arzneimittelforschung. 2010;60(6a):386-98.
Beshara et al., "Pharmacokinetics and red cell utilization of 52Fe/59Fe-labelled iron polymaltose in anaemic patients using positron emission tomography." Br J Haematol. Mar. 2003;120(5):853-9.
Bingham et al., "Increased transfer of iron to the fetus after total dose infusion of iron dextran during pregnancy." J Clin Pathol. Aug. 1983;36(8):907-9.
British Pharmacopoeia, Entry for Iron Dextran Injection, 2002;2:2252-2253.
C57BL/6 Mice Nomenclature: C57BL/6NCrl, Charles River Laboratories International, Inc. Pamphlet, 2011:4 pages.
Caligur, Dextran and Related Polysaccharides, BioFiles 2008;3(10):17.
Certificate of Analysis, Anaemex 100 mL HDPE vials, Jan. 14, 1998, 1 page.
Chandler et al., "Intravenous Iron Sucrose: Establishing a Safe Dose." Am J Kidney Dis. Nov. 2001;38(5):988-91.
Chertow et al., "On the relative safety of parenteral iron formulations." Nephrol Dial Transplant. Jun. 2004;19(6):1571-5.
Cisar et al., "Binding properties of immunoglobulin combining sites specific for terminal or nonterminal antigenic determinants in dextran." J Exp Med. Aug. 1, 1975;142(2):435-59.
Comparative Test vs. U.S. Pat. No. 3,639,588, Feb. 2, 2018, 2 pages.
CosmoFer® Summary of Product Characteristics (SmPC), Sep. 2003, 10 pages.
CosmoFer® Summary of Product Characteristics, Dec. 2005, 13 pages.
CosmoFer® UK Product Leaflet, 2001.
Crichton et al., "Iron Therapy with Special Emphasis on Intravenous Administration, UNI-MED." 2nd Ed., cover page, foreword, acknowledgements, preface and contents; and chapters 7, 9, 10 and 11, 40 pages (2005).

(56) References Cited

OTHER PUBLICATIONS

Danielson B.G., "Structure, chemistry, and pharmacokinetics of intravenous iron agents." J Am Soc Nephrol. Dec. 2004;15 Suppl 2:S93-8.
Dexferrum® (Iron dextran injection, USP) Rx Only, NDA 40-024/S-022, American Regent, Inc., pp. 3-11; retrieved on Jun. 19, 2019 from: <URL: https://www.accessdata.fda.gov/drugsatfda_docs/label/20091040024s022lb1.pdf>, 9 pages.
Dextran 1 for Injection, European Pharmacoepoeia 5.0, pp. 1408-1409; 2015.
Egeli et al., "An evaluation of iron-dextran supplementation in piglets administered by injection on the first, third or fourth day afterbirth." Res Vet Sci. Jun. 1999;66(3):179-84.
Elephants, San Diego Zoo Animals [online], retrieved on Jun. 13, 2016 from: <URL: http://animals.sandiegozoo.org/animals/elephant>, 3 pages.
EMEA Science Medicines Health, CHMP Assessment Report: Rienso, Common name: Ferumoxytol, dated Apr. 19, 2012, 79 pages.
Eschbach et al., "NKF-K/DOQI clinical practice guidelines for anemia of chronic kidney disease" Update 2000, Am J Kidney Dis, 2001, pp. S182-S238, vol. 37, Supp. 1.
Excerpt from Der Bund, edition of Apr. 13, 2005.
Executive Bios, Luitpold Pharmaceuticals [online], retrieved on Oct. 7, 2015 from: <URL: luitpold.com/ExecutiveBios.aspx>, 4 pages.
Extract from ClinicalTrials.gov website showing the details of trial No. NCT00396292, entitled 'Comparison of the Safety and Efficacy of Intravenous Iron Versus Oral Iron in Subjects Who Display Postpartum Anemia', last updated Feb. 5, 2018, 16 pages.
Extract from ClinicalTrials.gov website showing the details of trial No. NCT02397057 for the treatment of Restless Legs Syndrome, entitled Placebo-Controlled Study to Investigate the Efficacy & Safety of Injectafer in the Treatment of RLS, last updated Jan. 24, 2018, 8 pages.
Extract of MHRA Public Assessment Report for Ferinject® 50mg iron/ml solution for injection/infusion (Ferric carboxymaltose), 6 pages; retrieved on Jun. 19, 2019 from: <URL: http://www.mhra.gov.tdc/home/groups/par/documents/websiteresources/con014025.pdf>, pp. 1-6.
FDA Drug Safety Communication: FDA strengthens warnings and changes prescribing instructions to decrease the risk of serious allergic reactions with anemia drug Feraheme (ferumoxytol), Mar. 30, 2015, 4 pages.
Feraheme: ferumoxytol injection, revised Mar. 2015, AMAG Pharmaceuticals, Inc. Pamphlet, 4 pages.
Ferrosig: Iron polymaltose 50 mg/ml Drug Product Data Sheet, Zuellig Pharma Limited, prepared Jul. 10, 2003, 6 pages.
Fielding, "Intravenous iron-dextrin in iron-deficiency anaemia." British Medical Journal, Jul. 29, 1961;2(5247):279.
Fishbane, "Safety in iron management." Am J Kidney Dis, Jun. 1, 2003;41:18-26.
Fisons Pharmaceuticals, Imferon, US drug monograph, 1989, 2 pages.
Folb, P. I., "The safety of iron dextran and a comparison with iron sucrose for intravenous use: a short report to the World Health Organization Advisory Committee on the safety of medicines." dated Oct. 18, 2004, 5 pages.
Funk et al., Physical and Chemical Characterization of Therapeutic Iron Containing Materials: A Study of Several Supraparamagnetic Drug Formulations with the p-FeOOH or Ferrihydrite Structure, Hyperfine Interactions 136, 73-95 (2001).
Funk et al., "The new generation of intravenous iron: chemistry, pharmacology, and toxicology of ferric carboxymaltose." Arzneimittelforschung. 2010;60(6a):345-53.
Galenica Ltd., "Venofer® approved by FDA ahead of company expectations for use in USA for treatment of iron deficiency anemia in pre-dialysis patients." published Jun. 20, 2005 [online], retrieved on Jun. 19, 2019, from <URL:http://www.evaluategroup.com/Universal/View.aspx?type=Story&id=140890>) 1 page.

Geisser et al., "Investigation on the Dosage/Efficacy Relationship of Iron Dextran in Veal Calves." Arzneimittelforschung. Jan. 1991;41(1):32-7.
Geisser et al., "Structure/Histotoxicity Relationship of Parenteral Iron Preparations, Drug Research." Arzneimittelforschung. Dec. 1992;42(12):1439-52.
Gleptosil Injection (Canada), [cited Nov. 15, 2017]; available from: <URL:drugs.com/vet/gleptosil-injection-can.html, 3 pages.
Grimes et al., "Metabolism of $^{59}$Fe-dextran complex in human subjects." Br Med J. Nov. 9, 1957:2(5053):1074-7.
Guidelines for administration of IV iron polymaltose in chronic kidney disease via continuous intravenous infusion, Royal Perth Hospital, Mar. 2002, 3 pages.
Gupte et al., "Iron Deficiency Anemia: Management and Prevention in Children." JK Science, 2001:3(4); 160-165.
Haines et al., "Delayed adverse reactions to total-dose intravenous iron polymaltose." Intern Med J. Apr. 2009;39(4):252-5.
Hamstra et al., "Intravenous Iron Dextran in Clinical Medicine." JAMA. May 2, 1980;243(17):1726-31.
Hood et al., "The Safety of Intravenous Iron Dextran (Dexferrum®) During Hemodialysis in Patients with End Stage Renal Disease." Nephrol Nurs J. Feb. 2000;27(1):41-2.
INFed (iron dextran injection, USP), Schein Pharmaceutical, Inc., revised Sep. 1996, 2 pages.
Injectafer® (ferric carboxy-maltose injection), American Regent, Inc., Pamphlet revised Jul. 2013, 11 pages.
Jahn et al., "A comparative study of the physiochemical properties of iron isomaltoside 1000 (Monofer), a new intravenous iron preparation and its clinical implications." Eur J Phann Biopharm. Aug. 2011;78(3):480-91.
Johansson et al., "Intravenous iron isomaltoside 1000 (Monofer®) reduces postoperative anaemia in preoperatively non-anaemic patients undergoing elective or subacute coronary artery bypass graft, valve replacement or a combination thereof: a randomized double-blind placebo-controlled clinical trial (the PROTECT trial)." Vox Sang. Oct. 2015;109(3):257-66.
Kabat et al. "Dextran—An Antigen in Man." J Immunol. Jun. 1953;70(6):514-32.
Kalra et al, Iron isomaltoside 1000: a new high dose option for parenteral iron therapy, Port. J. Hypert. Jan. 2012;26(1):13-24.
Keating, G. M., "Ferric Carboxymaltose: A Review of its Use in Iron Deficiency." Drugs Jan. 2015;75(1):101-27.
Kudasheva et al., "Structure of carbohydrate-bound polynuclear iron oxyhydroxide nanoparticles in parenteral formulations." J Inorg Biochem. Nov. 2004;98(11):1757-69.
Kulnigg et al., "A novel intravenous iron formulation for treatment of anemia in inflammatory bowel disease: the ferric carboxymaltose (FERINJECT) randomized controlled trial." Am J Gastroenterol. May 2008;103(5):1182-92.
Lam-Po-Tang et al., "Icodextrin Hypersensitivity in a CAPD Patient." Perit Dial Int. Jan.-Feb. 1997;17(1):82-4.
Landry et al., "Pharmacokinetic study of Fentmoxytol: A New Iron Replacement Therapy in Normal Subjects and Hemodialysis Patients." Am J Nephrol. Jul.-Aug. 2005;25(4):400-10.
Leuillet et al. "Sur L'Utilisation D'Un Compose De Fer Dextrane Hydrogene Par Injection Chez La Truie En Gestation Et En Lactation." Ann. Zootech. 1968, 17(I), 59-70, 12 pages (with Certified English language translation).
Lindvall and Andersson, "Studies on a new intramuscular haematinic, iron-sorbitol." Br J Pharmacol Chemother. Dec. 1961:17:358-71.
Linhardt et al., "Production and Chemical Processing of Low Molecular Weight Heparins." Semin Thromb Hemost. 1999;25 Suppl 3:5-16.
London, E., "The molecular formula and proposed structure of the iron-dextran complex, Imferon." J Pharm Sci. Jul. 2004;93(7):1838-46.
Luitpold Press Release, American Regent announces a new FDA-Approved Pediatric Indication for Venofer® (Iron Sucrose Injection, USP), Published Sep. 26, 2012.
Luitpold Press Release, American Regent Announces an FDA-Approved Pediatric Indication Exclusivity for Venofer (Iron Sucrose Injection, USP), Published Oct. 19, 2012.

(56) References Cited

OTHER PUBLICATIONS

Luitpold Press Release, American Regent announces FDA approval for Venofer® in the treatment of Iron Deficiency Anemia in Peritoneal Dialysis Patients, Published Oct. 17, 2005.
Luitpold Press Release, American Regent announces new PDUFA action date for Injectafer® (ferric carboxymaltose injection) NDA for the treatment of iron deficiency anemia, Published Apr. 8, 2013.
Luitpold Press Release, American Regent Resumes Shipment of Injectable Products, Published May 6, 2011.
Luitpold Press Release, American Regent Resumes Shipment of Venofer® (iron sucrose injection, USP), Published May 3, 2011.
Luitpold Press Release, American Regent's Injectafer® (Ferric Carboxymaltose Injection) Assigned Q Code by Centers for Medicare and Medicaid Services, Published May 1, 2014.
Luitpold Press Release, FDA Advisory Committee Supports Favorable Risk-Benefit Profile for Injectafer™ (Ferric Carboxymaltose Injection) Under Certain Indications Published Feb. 4, 2008.
Luitpold Press Release, FDA Assigns PDUFA Date for Injectafer® (ferric carboxymaltose injection) NDA, Published Dec. 15, 2011.
Luitpold Press Release, Important Drug Product Notice: Luitpold Pharmaceuticals, Inc. Announces Temporary Suspension of Distribution and Manufacture of Drug Products, Published Apr. 21, 2011.
Luitpold Press Release, Injectafer® (ferric carboxymaltose injection) receives US FDA approval for the treatment of Iron Deficiency Anemia, Published Jul. 25, 2013.
Luitpold Press Release, Luitpold Pharmaceutical's INJECTAFER™ (ferric carboxymaltose injection) receives non-approvable letter from FDA, Published Mar. 12, 2008.
Luitpold Press Release, Luitpold Pharmaceuticals, Inc. Receives Complete Response Letter for Injectafer® from the U.S. Food and Drug Administration, Published Jul. 26, 2012.
Luitpold Press Release, Luitpold Pharmaceuticals, Inc. Submits Injectafer® NDA to the U.S. Food and Drug Administration, Published Oct. 13, 2011.
Luitpold Press Release, Luitpold Pharmaceuticals/American Regent and Fresenius Medical Care sign agreements for exclusive sublicense of Venofer® in U.S., Published Jul. 9, 2008.
Luitpold Press Release, Luitpold Pharmaceuticals/American Regent announces Closing of exclusive sublicense of Venofer® by Fresenius Medical Care in U.S., Published Sep. 16, 2008.
Luitpold Press Release, Venofer® (iron sucrose injection, USP) receives FDA approval for the treatment of iron deficiency anemia in pre-dialysis patients, American Regent, Jun. 17, 2005.
Lyseng-Williamson et al., "Ferric Carboxymaltose—A Review of its Use in Iron-Deficiency Anaemia, Drugs." 2009:69(6):739-56.
MacDougall et al., "Use of intravenous iron supplementation in chronic kidney disease." Iran J Kidney Dis. Jan. 2013;7(1):9-22.
Macdougall, "Intravenous administration of iron in epoetin-treated haemodialysis patients—which drugs, which regimen?" Nephrol Dial Transplant. Nov. 2000;15(11):1743-5.
MacDougall, "Strategies for iron supplementation: Oral versus intravenous." Kidney Int Suppl. Mar. 1999;69:S61-6.
Mamula et al., "Total Dose Intravenous Infusion of Iron Dextran for Iron-Deficiency Anemia in Children With Inflammatory Bowel Disease." J Pediatr Gastroenterol Nutr. Mar. 2002;34(3):286-90.
Manley et al., "Determination of VIT 45 (IND#63,243—American Regent) removal by closed loop in vitro hemodialysis system." Int J Artif Organs. Nov. 2006;29(11):1062-6.
Marchasin et al., "The Treatment of Iron-Deficiency Anemia with Intravenous Iron Dextran." Blood. Mar. 1964;23:354-8.
McCurdy et al., "Parenteral Iron Therapy With Special Reference to a New Preparation for Intramuscular Injection." N Engl J Med. Dec. 12, 1957;257(24):1147-53.
McNaught, "Nomenclature of Carbohydrates." Pure & Appl. Chem., Jan. 1, 1996;68(10):1919-2008.
Mehmood et al.,"Response to intravenous iron in patients with iron deficiency anemia (IDA) and restless leg syndrome (Willis-Ekbom disease)." Sleep Med. Dec. 2014;15(12):1473-6.
Monofer Summary of Product Characteristics, revised Mar. 10, 2014, 5 pages.

Morris et al., "Conformation and Intermolecular Interactions of Carbohydrate Chains." J Supramol Struct. 1977;6(2):259-74.
National Kidney Foundation, KDOQI Clinical Practice Guidelines and Clinical Practice Recommendations for Anemia in Chronic Kidney Disease, Am. J. Kidney Dis. 47(5), S1-S145 (suppl 3) (2006).
National Kidney Foundation, NKF-K/DOQI Clinical Practice Guidelines for Hemodialysis Adequacy: Update 2000, Am. J. Kidney Dis. 37, S7-S64 (suppl 1) (2001).
NDA 22-054 for Injectafer (Ferric Carboxymaltose) for the treatment of iron deficiency anemia in patients with heavy uterine bleeding or postpartum patients, FDA Advisory Committee Briefing Document: Drug Safety and Risk Management Committee, Feb. 1, 2008, 63 pages.
Neiser et al., Assessment of dextran antigenicity of intravenous iron products by an immunodiffusion assay, Port. J. Nephroi Hypert. 2011;25(3):219-4.
Neiser et al., Physico-chemical properties of the new generation IV iron preparations ferumoxytol, iron isomaltoside 1000 and ferric carboxymaltose, Biometals, published online Mar. 24, 2015, doi: 10.1007/s10534-015-9845-9, 21 pages.
Neiser et al., Reply to the letter to the editor by Johannes Ring and Rudi Valenta on the article Assessment of dextran antigenicity of intravenous iron products by an immunodiffusion assay, Port. J. Hypert. 2012, 26(4), 311-312.
Newnham et al., :Safety of iron polymaltose given as a total dose iron infusion. Intern Med J. Oct. 2006;36(10):672-4.
Nissenson et al., "Controversies in iron management." Kidney Int Suppl. Nov. 2003;(87):S64-71.
Nissim, J.A., "Deposition of Iron in the Testes After Administration of an Iron-dextran Complex." Lancet. Apr. 2, 1955;268(6866):701-2.
Orange Book: Approved Drug Products with Therapeutic Equivalence Evaluations, [cited Nov. 21, 2017]; [online] available from: <URL:accessdata.fda.gov/scripts/cder/ob/patentinfo.cfm?Product No=001&Appl No=0221 . . . , 3 pages.
Orange Book: Approved Drug Products with Therapeutic Equivalence Evaluations, Ferumoxytol, [online] retrieved on Mar. 9, 2015.
Orange Book: Approved Drug Products with Therapeutic Equivalence Evaluations, Ferric Carboxymaltose, [online] retrieved on Mar. 9, 2015.
Parham, P., The Immune System. Chapter 1: Elements of the immune system and their roles in defense, Garland Publishing/Elsevier Science Ltd., 2000, pp. 1-30.
Paschen, H. W., "Effective anemia treatment involving the administration of high intravenous doses of iron." Geburtshilfe Frauenheilkunde 1949, 9, 604-616 [Original document in German and English language translation].
Paul et al., "Synthesis of Ultrasmall Superparamagnetic Iron Oxides Using Reduced Polysaccharides." Bioconjug Chem. Mar.-Apr. 2004;15(2):394-401.
Peacock et al., "Clinical Practice Guidelines for Maintaining Adequate Iron Status With Intravenous Iron Dextran in Hemodialysis Patients." ANNA J. Jun. 1999;26(3):337-43.
Pink Sheet, Pharma Intelligence, "Fisons' Opticrom, Imferon May Be Off U.S. Market Until Late 1992 as the company upgrades U.K. manufacturing plant to meet FDA quality control concerns", [online] retrieved on Jun. 13, 2016 from <URL:pharmamedtechbi.com/publications/the-pink-sheet/53/051/fisons-opticrom-imferon-may-be-off-us-market-until-late-1992-as-the-company-upgrade . . . >, posted Dec. 23, 1991, 3 pages.
Polysaccharide Nomenclature. Pure & Appl. Chem., 1982:54(8), 1523-1526.
Preusser et al., "Effects of intravenous ABT-870 (iron (III)-hydroxide oligosaccharide) on mean arterial pressure and heart rate in the anaesthetized beagle: comparison with other iron-containing heamatinic agents." Clin Exp Pharmacol Physiol. Dec. 2005;32(12):1020-6.
Promit® dextran 1: Consumer Medicine Information, [online] retrieved from <URL:mydr.com.au/cmis/promit-injection>, dated Feb. 7, 2003, Published by MIMS Apr. 2005, 2 pages.

(56) References Cited

OTHER PUBLICATIONS

Pugh-Clarke et al., "An Evidence-Based Approach to Anaemia Management in Predialysis Chronic Kidney Disease." J Ren Care. Dec. 2009;35 Suppl 2:29-31.
Reinisch et al., "A 1-year trial of repeated high-dose intravenous iron isomaltoside 1000 to maintain stable hemoglobin levels in inflammatory bowel disease." Scand J Gastroenterol. 2015;50(10):1226-33.
Reinisch et al., "A randomized, open-label, non-inferiority study of intravenous iron isomaltoside 1,000 (Monofer) compared with oral iron for treatment of anemia in IBD (PROCEED)." Am J Gastroenterol. Dec. 2013;108(12):1877-88.
Report of the ACS Carbohydrate Division Nomenclature Committee, presented at the Annual Meeting of the ACS Committee on Nomenclature, Terminology and Symbols, Apr. 7, 2008, New Orleans.
Research Subject Information and Consent Form, entitled „Evaluation of the safety, tolerability and pharmacokinetic profiles of single rising doses and increasing administration rates of ABT-870 in ESRD subjects on chronic hemodialysis with iron deficiency anemia, Sponsored by Abbott Laboratories, dated Apr. 30, 2004, 10 pages.
Richter, A. W., Immune Complex Anaphylaxis Induced by Dextran and its Elimination by Hapten Inhibition, in New Trends in Allergy II, J. Ring et al. (eds.), Springer-Verlag Berlin Heidelberg, 1986, pp. 272-283.
Ring and Valenta, Letter and Reply to: Neiser et al. (2011) Assessment of dextran antigenicity of intravenous iron products by an immunodiffusion assay, Port. J. Nephrol. Hypert. 2012:26(4), 3 pages.
Roe, F. J. C, On Potential Carcinogenecity of the Iron Macromolecular Complexes, UICC Monograph Series: Potential Carcinogenic Hazards from Drugs 7, 1967, pp. 105-116.
Safety Data Sheet, Dextran T1 Technical Quality, retrieved on May 27, 2015 from: <URL:dextran.net/products/technical-quality/c-24/c-74>, 6 pages.
Screenshot of Luitpold Pharmaceuticals homepage (URL:luitpold.com/), showing the relationship between Luitpold and American Regent Inc., 1 page, May 6, 2018.
Screenshot showing document properties of the reproduction of the speech given by Dr. Barbara von Eisenhart-Rothe entitled Clinical Development Programme of VIT-45, given at a Press conference on Apr. 12, 2005, 2 pages.
Screenshot showing results of Google search for eisenhart rothe vit-45, Apr. 13, 2017.
Seid et al., Blood 108(11):3739 (2006), obtained from the British Library with a public availability date stamp and covering letter showing availability to the public on Dec. 6, 2006, 6 pages.
Seid et al., Safety Profile of Iron Carboxymaltose, a New High Dose Intravenous Iron in Patients with Iron Deficiency Anemia, Blood 2006:108(11), 3739, 4 pages.
Sergejew et al., "Chelator-induced iron excretion in iron-overloaded marmosets." Br J Haematol. Sep. 2000;110(4):985-92.
Silverberg et al., "Erythropoietin should be part of congestive heart failure management." Kidney Int Suppl. Nov. 2003;(87):S40-7.
Silverberg et al., "The role of anemia in the progression of congestive heart failure. Is there a place for erythropoietin and intravenous iron?" J Nephrol. Nov.-Dec. 2004;17(6):749-61.
Singh et al., "A comparison between intravenous iron polymaltose complex (Ferrus Hausmann®) and oral ferrous fumarate in the treatment of iron deficiency anaemia in pregnancy." Eur J Haematol. Feb. 1998;60(2):119-24.
Sipe et al., "Brain iron metabolism and neurodegenerative disorders." Dev Neurosci. 2002;24(2-3):188-96.
Sofic et al., "Increased iron (III) and total iron content in post mortem substantia nigra of parkinsonian brain." J Neural Transm. 1988;74(3):199-205.
Speech given by Dr. Barbara von Eisenhart-Rothe at Galenica Press Conference 5005 on Apr. 12, 2005, Subject: Clinical Development Programme of VIT-45, 3 pages.

Spinowitz et al., The safety and efficacy of ferumoxytol therapy in anemic chronic kidney disease patients, Kidney Int. Oct. 2005;68(4):1801-7.
Syner-Med, Summary of Product Characteristics; Ferinject, 2009, 8 pages.
Tagboto et al, "The efficacy of a single dose of intravenous ferric carboxymaltose (Ferinject®) on Anaemia in a pre-dialysis population of chronic kidney disease patients." J Ren Care. Mar. 2009;35(1):18-23.
Test for Iron Absorption, British Pharmacopoeia, 1968, p. 1364.
The Merck Index: An Encylopedia of Chemicals, Drugs and Biologicals, 14th Edition, O'Neil et al. editors, Merck Research Laboratories, 2006, pp. 501-502.
UBS Report on Galenica's Financial Results, dated Apr. 15, 2004, 15 pages.
Ullmann's Encyclopedia of Industrial Chemistry, 1987, Fifth Edition, vol. A8, pp. 449-454.
Ullmann's Encyclopedia of Industrial Chemistry, 2003, Sixth Edition, vol. 10, pp. 435-440.
USP28-NF23, Official Monographs/Dextran, 2004, pp. 601-602, The United States Pharmacopeial Convention, Inc.
Van Wyck et al., "Labile iron in parenteral iron formulations: a quantitative and comparative study." Nephrol Dial Transplant. Mar. 2004;19(3):561-5.
Van Wyck et al., "A randomized, controlled trial comparing IV iron sucrose to oral iron in anemic patients with nondialysis-dependent CKD." Kidney Int. Dec. 2005;68(6):2846-56.
Van Wyck et al., "Intravenous Ferric Carboxymaltose Compared with Oral Iron in the Treatment of Postpartum Anemia." Obstet Gynecol. Aug. 2007;110(2 Pt 1):267-78.
Van Wyck et al., "Making sense: a scientific approach to intravenous iron therapy." J Am Soc Nephrol. Dec. 2004;15 Suppl 2:S91-2.
Van Wyck, "Labile iron: manifestations and clinical implications." J Am Soc Nephrol. Dec. 2004;15 Suppl 2:S107-11.
van Zyl-Smit R. et al., "Experience with the Use of an Iron Polymaltose (Dextrin) Complex Given by Single Total Dose Infusion to Stable Chronic Haemodialysis Patients." Nephron. Oct. 2002;92(2):316-23.
Vollhardt and Schore, Organic Chemistry Structure and Function. Chapter 24: Carbohydrates Polyfunctional Compounds in Nature, Fifth Edition, W.H. Freeman and Company, New York, 2007, pp. 1096-1138.
Wallerstein, R. O., "Intravenous Iron-Dextran Complex." Blood. Oct. 1968;32(4):690-5.
Walters et al., "Benchmarking iron dextran sensitivity: reactions requiring resuscitative medication in incident and prevalent patients." Nephrol Dial Transplant. Jul. 2005;20(7):1438-42.
Wang et al., "Comparative Risk of Anaphylactic Reactions Associated with Intavenous Iron Products." JAMA. Nov. 17, 2015;314(19):2062-8.
Wang et al., "Supplementary Online Content for Comparative Risk of Anaphylactic Reactions Associated with Intravenous Iron Products." JAMA Nov. 17, 2015;314(19):2062-8.
Zager et al, "Parenteral iron nephrotoxicity: Potential mechanisms and consequences." Kidney Int. Jul. 2004;66(1):144-56.
Zhang et al., "Tandem MS can Distinguish Hyaluronic Acid from N-Acetylheparosan." J Am Soc Mass Spectrom. Jan. 2008;19(1):82-90.
Affadavit of Hans Berg Andreasen, filed in the Post-Grant Opposition of Indian Patent No. 291100 (Appl. No. 8145/DELNP/2011), 2019. 7 pages.
Affadavit of Dr. Klaus Bock, filed in the Post-Grant Opposition of Indian Patent No. 291100 (Appl. No. 8145/DELNP/2011), 2019. 32 pages.
Jones, R. et al. "Kinetics of Hydrolysis of Isomaltotriose and Isomaltotriitol" JACS (1955 vol. 77, pp. 1659-1663.
Shimamura, A. et al. "Assignment of $^{13}$C-n.m.r. signals for reduced isomaltooligosaccharides," Carbohyd. Res., vol. 220, pp. 243-248. 1991.
"Clinical trials for monofer." EU Clinical Trials Register, retreived Jul. 24, 2018 from URL: https://www.clinicaltrialsregister.eu/ctr-search/search?query=monofer&page=2.

(56) References Cited

OTHER PUBLICATIONS

"Isomaltose" printout from PubChem, U.S. National Library of Medicine, retreived Dec. 13, 2018 from URL: https://pubchem.ncbi.nlm.nih.gov/compound/isomaltose#section=Top.

Allen et al. "Clinical efficacy and safety of IV ferric carboxymaltose (FCM) treatment of RLS: a multi-centred, placebo-controlled preliminary clinical trial." Sleep medicine. Oct. 1, 2011;12(9):906-13.

Allen et al. "MRI measurement of brain iron in patients with restless legs syndrome." Neurology. Jan. 23, 2001;56(2):263-5.

Allen et al. "Restless legs syndrome: a review of clinical and pathophysiologic features." J Clin Neurophysiol. Mar. 2001;18(2):128-47.

Archibald RM, Hancock EE. "Iron Deficiency as the Probable Cause of Stillbirth in Swine." Can J Comp Med. May 1939;3(5):134.

Astrakas et al. "T2 relaxometry and fMRI of the brain in late-onset restless legs syndrome." Neurology. Sep. 16, 2008;71(12):91 1-6.

Auvigne et al. "Anaemia in the hyperprolific sow: Effect of injectable iron administration and relation with fattening score." InProceedings of the 21st IPVS Congress, Vancouver, Canada 2010.

Bastian et al. "Perinatal iron and copper deficiencies alter neonatal rat circulating and brain thyroid hormone concentrations." Endocrinology. Jun. 23, 2010;151(8):4055-65.

Bianco et al. "Iron deficiency alters dopamine uptake and response to L-DOPA injection in Sprague—Dawley rats." J Neurochem. Jul. 2008;106(1):205-15.

Bille et al. "Preweaning mortality in pigs. 2. The perinatal period." Nord Vet Med. May 1974;26(5):294-313.

Connor et al. "Altered dopaminergic profile in the putamen and substantia nigra in restless leg syndrome." Brain. May 25, 2009;132(9):2403-12.

Connor et al. "Neuropathological examination suggests impaired brain iron acquisition in restless legs syndrome." Neurology. Aug. 12, 2003;61(3):304-9.

Danish Search Report for priority Int'l Appl. No. PA 2015 70380, in search report completed Jan. 21, 2016.

Earley et al. "A randomized, double-blind, placebo-controlled trial of intravenous iron sucrose in restless legs syndrome." Sleep Med. Feb. 2009;10(2):206-11.

Earley et al. "Abnormalities in CSF concentrations of ferritin and transferrin in restless legs syndrome." Neurology. Apr. 25, 2000;54(8):1698-700.

Earley et al. "MRI-determined regional brain iron concentrations in early-and late-onset restless legs syndrome." Sleep Med. Aug. 2006;7(5):458-61.

Earley et al. "Repeated IV doses of iron provides effective supplemental treatment of restless legs syndrome." Sleep Med. Jul. 2005;6(4):301-5.

Earley et al. "The treatment of restless legs syndrome with intravenous iron dextran." Sleep Med. May 2004;5(3):231-5.

Egeli et al. "The effect of peroral administration of amino acid-chelated iron to pregnant sows in preventing sow and piglet anaemia." Acta veterinaria Scandinavica. 1998;39(1):77-87.

E-register of Australian Patent Application No. 2009342799, retreived Dec. 24, 2018.

E-register of Australian Patent Application No. 28273/99, retreived Dec. 13, 2018.

E-register of Eurasian Patent Application No. 003427, retreived Dec. 13, 2018.

Goergieff MK. "The role of neurodevelopment: fetal iron deficiency and the developing hippocampus." Biochem Soc Trans. Dec. 2008;36(Pt 6):1267-71.

Grote et al. "A randomized, double-blind, placebo controlled, multi-center study of intravenous iron sucrose and placebo in the treatment of restless legs syndrome." Mov Disord. Jul. 30, 2009;24(10):1445-52.

Haba-Rubio et al. "Restless legs syndrome and low brain iron levels in patients with haemochromatosis." J Neurol Neurosurg Psychiatry. Jul. 2005;76(7):1009-10.

International Search Report for Int'l Appl. No. PCT/DK2015/050328, dated May 6, 2016.

International Search Report for Int'l Appl. No. PCT/DK2016/050216, dated Dec. 29, 2016.

International Search Report for Int'l Appl. No. PCT/EP2016/055758, dated Sep. 22, 2016.

Jensen, Anna Katherine; and Nielsen. Jens Peter. "Association between blood haemoglobin concentration in sows and neonatal piglets." HERD-centre, Dept. of Large Animal Sciences, University of Copenhagen, DK. May 22-24, 2013.

Lee et al. "In vivo measurement of iron deficiency in restless legs syndrome (rls) with voxel-based R2 relaxometry." InProc Intl Soc Mag Reson Med 2007 (vol. 15, p. 2170).

Leuillet et al. "Sur L'Utilisation D'Un Compose De Fer Dextrane Hydrogéné (1) Par Injection Chez La Truie En Gestation Et En Lactation." InAnnales de Zootechnie 1968 (vol. 17, No. 1, pp. 59-70).

Lozoff B. Iron deficiency and child development. Food Nutr Bull. Dec. 2007;28(4 Suppl):S560-71.

Lozoff et al. "Functional significance of early-life iron deficiency: outcomes at 25 years." The Journal of Pediatrics. Nov. 1, 2013;163(5):1260-6.

Lozoff et al. "Iron supplementation in infancy contributes to more adaptive behavior at 10 years of age." J Nutr. Apr. 9, 2014;144(6):838-45.

Macdougall et al. Use of Intravenous Iron Supplementation in Chronic Kidney Disease an Update. Iranian Journal of Kidney Diseases. Jan. 2013;7(1):9-22.

Molina et al. "Ingestion of Mn and Pb by rats during and after pregnancy alters iron metabolism and behavior in offspring." Neurotoxicology. Aug. 2011;32(4):413-22.

Monnot et al. "Regulation of brain copper homeostasis by the brain barrier systems: effects of Fe-overload and Fe-deficiency." Toxicology Appl Pharmacol. Nov. 1, 2011;256(3):249-57.

Monofer solution for injection or infusion. Scientific discussion for the approval of Monofer. Finalized Nov. 26, 2009.

Moore et al. "Iron deficiency anemia as a cause of stillbirths in swine." J Am Vet Med Assoc. Oct. 1, 1965;147(7):746-8.

Morris et al. "Reactive oxygen species and iron—a dangerous partnership in inflammation." Int J Biochem Cell Biol. Feb. 1995;27(2):109-22.

Myers et al. "Comparative efficacy and safety of intravenous ferric carboxymaltose (Ferinject) and iron (III) hydroxide dextran (Cosmofer) in pregnancy." Obstetric Medicine. Sep. 2012;5(3):105-7.

Myers et al. "Zinc transporters, mechanisms of action and therapeutic utility: implications for type 2 diabetes mellitus." J Nutr Metab. Dec. 12, 2012;2012.

Nordfjeld et al. "Pharmacokinetics of iron isomaltoside 1000 in patients with inflammatory bowel disease." Drug Des Devel Ther. 2012; 6"43-50.

O'Keeffe et al. "Iron status and restless legs syndrome in the elderly." Age Ageing. May 1994;23(3):200-3.

Oladiji TA. "Tissue levels of iron, copper, zinc and magnesium in iron deficient rats." Biokemistri. 2003;14(1):75-81.

Ondo WG. "Intravenous iron dextran for severe refractory restless legs syndrome." Sleep Med. May 2010;1 1(5):494-6.

Pedroso et al. "Severity of restless legs syndrome is inversely correlated with echogenicity of the substantia nigra in different neurodegenerative movement disorders." J Neurol Sci. Aug. 15, 2012;319(1-2):59-62.

Piñero et al. "The intracellular location of iron regulatory proteins is altered as a function of iron status in cell cultures and rat brain." J Nutr. Nov. 2001;1 31(11):2831-6.

Randall et al. "Stillbirths in Pigs-Possible Role of Anoxia." Veterinary Record. Jan. 1, 1967;81(14):359.

Response to Notice of Opposition filed agaisnt European case EP1066056 filed Sep. 8, 2003.

Rizzo et al. "Low brain iron content in idiopathic restless legs syndrome patients detected by phase imaging." Mov Disord. Nov. 2013;28(13):1886-90.

Rootwelt et al. "Associations between intrapartum death and piglet, placental, and umbilical characteristics." J Anim Sci. Dec. 2012;90(12):4289-96.

(56) References Cited

OTHER PUBLICATIONS

Sakai et al. "The preventive effect of dietary iron-D, L-threonine supplement on anemia in young pigs." Bulletin of the College of Agriculture and Veterinary Medicine—Nihon University (Japan) (1986).
Sampaio et al. "Iron toxicity mediated by oxidative tissue damage in an animal model of diabetes." Biometals. Apr. 2014;27(2):349-61.
Scholl TO. "Iron status during pregnancy: setting the stage for mother and infant." The American Journal of Clinical Nutrition. Am J Clin Nutr. May 2005;81(5):1218S-1222S.
Seid et al. "Ferric carboxymaltose injection in the treatment of postpartum iron deficiency anemia: a randomized controlled clinical trial." Am J Obstet Gynecol. Oct. 2008;199(4):435.e1-7.
Sloand et al. "A double-blind, placebo-controlled trial of intravenous iron dextran therapy in patients with ESRD and restless legs syndrome." Am J Kidney Dis. Apr. 2004:43(4):663-70.
Snyder et al. "Mitochondrial ferritin in the substantia nigra in restless legs syndrome." J Neuropathol Exp Neurol. Nov. 2009;68(11):1193-9.
Sun et al. "Iron and the restless legs syndrome." Sleep. Jun. 1, 1998;21(4):381-7.
Svetina et al. "Relation between erythrocyte parameters and stillbirth in piglets." Veterinarski arhiv. Aug. 20, 2006;76(4):297-303.
Thorn CE. Hematology of the pig. Schalm's Veterinary Hematology. 6th ed. Ames: Wiley-Blackwell. 2010:843-51.
Toblli et al. "Effects of iron deficiency anemia and its treatment with iron polymaltose complex in pregnant rats, their fetuses and placentas: oxidative stress markers and pregnancy outcome." Placenta. Feb. 1, 2012;33(2):81-7.
Trenkwalder et al. "Treatment of restless legs syndrome: an evidence-based review and implications for clinical practice." Mov Disord. Dec. 15, 2008:23(16):2267-302.
Unger et al. "Effects of IV iron isomaltoside-1000 treatment on regional brain iron status in an iron-deficient animal." Neuroscience. Aug. 29, 2013;246:179-85.
Vinther, Jens. "National Average for Productivity in Pork Production 2012." (including English translation) Videncenter for Svineproduktion. 2013.
Wei et al. "Effects of iron from an amino acid complex on the iron status of neonatal and suckling piglets." Asian-Australasian Journal of Animal Sciences. Dec. 2, 2005;18(10):1485-91.
Zaleski et al. "Variables related to the progress of parturition and probability of stillbirth in swine." Can Vet J. Feb. 2003;34(2):109-13.
Zariwala et al. "A novel approach to oral iron delivery using ferrous sulphate loaded solid lipid nanoparticles." Int J Pharm. Nov. 18, 2013;456(2):400-7.
Granted specification, including claims of Indian Patent No. 224635 issued Oct. 30, 2008. 20 pages.
"Reflection paper on the data requirements for intravenous iron-based nano-colloidal products developed with reference to an innovator medicinal product", Mar. 26, 2015, Committee for Medicinal Products for Human Use (CHMP). (10 pages).
Heath et al., "Quantitative Aspects of Iron Deficiency in Hypochromic Anemia (The Parenteral Administration of Iron)," J Clin Invest. Nov. 1932;11(6):1293-312. (20 pages).
"Monofer 100 mg/ml solution for injection/infusion," Summary of Product Characteristics, Jun. 9, 2017. (7 pages).
Synopsis of clinical trial report dated Oct. 10, 2008 pertaining to Monofer. (6 pages).
About the EU Clinical Trials Register, retrieved May 17, 2019. (2 pages).
Extract from United States Pharmacopoeia, Jan. 1, 1995, pp. 1957-1959. (4 pages).
"Declaration of Hans Berg Andreasen" dated May 16, 2018. (2 pages).

\* cited by examiner

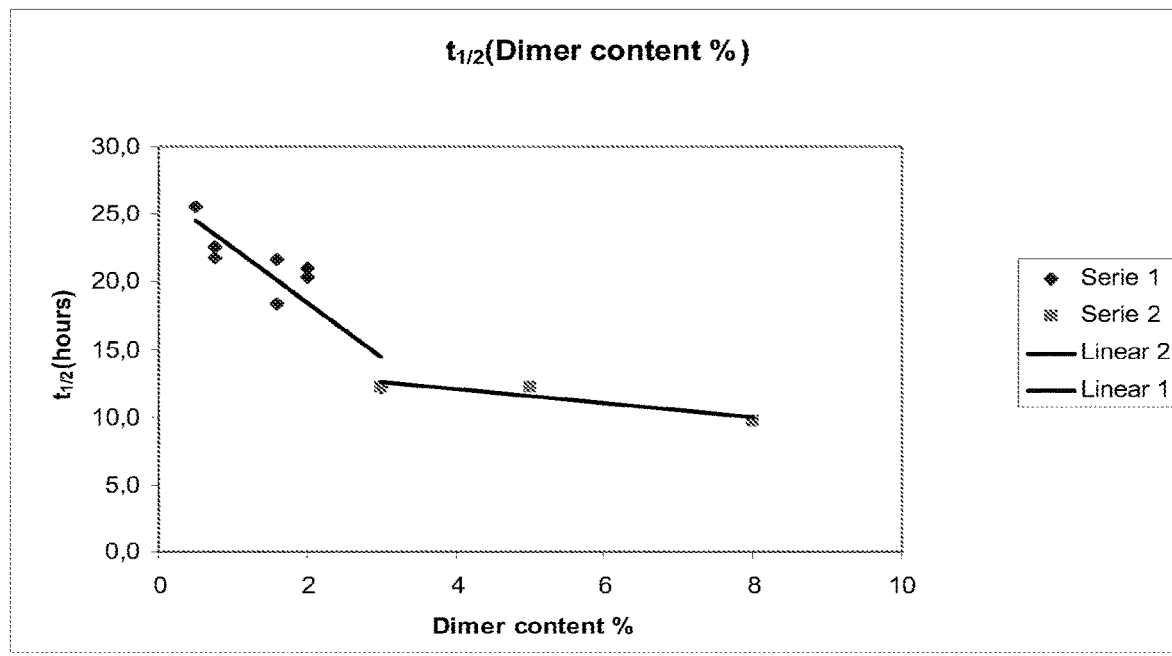

STABLE IRON OLIGOSACCHARIDE COMPOUND

CROSS-REFERENCE TO RELATED APPLICATIONS

The present application is a divisional under 35 U.S.C. § 121 of U.S. application Ser. No. 14/307,957, filed on Jun. 18, 2014, now U.S. Pat. No. 9,439,969 which is a divisional under 35 U.S.C. § 121 of U.S. application Ser. No. 13/138, 669, filed on Sep. 16, 2011, now U.S. Pat. No. 8,815,301, which is a National Phase Application under 35 U.S.C. § 371 of PCT/DK2009/050069, filed on Mar. 25, 2009, the entire contents of each of which are incorporated herein by reference.

The present invention relates in a first aspect to an iron oligosaccharide compound with improved stability. In a second aspect, the invention relates to a process for preparing the iron oligosaccharide compound according to the first aspect of the invention. Further, in a third aspect the invention relates to the use of said compound for preparation of a composition for treatment of iron deficiency anaemia.

Due to its widespread occurrence, iron-deficiency anaemia remains a global health issue of major concern. In humans and domestic animals alike it is one of the most frequently observed pathological conditions.

Although iron-deficiency anaemia can often be prevented or cured by oral administration of iron-containing preparations, it is in many cases preferred to use parenterally administrable iron preparations to avoid variations in bio-availability of oral administrations and to ensure effective administration.

Therefore, iron-containing preparations for parenteral use, i.e. subcutaneous, intramuscular or intravenous administration, have for many years been at the disposal of the veterinary or human medical practitioner.

Although various iron-containing substances have been used or suggested as components in parenterally injectable preparations against iron-deficiency anaemia, the most common preparations accepted today are such which comprise a combined product of ferric oxyhydroxide (or ferric hydroxide) in association with a saccharide, notably dextran or dextrin. Dextran is a polymeric carbohydrate produced by the microorganism *Leuconostoc mesenteroides*, while dextrin is a depolymerisation product of starch.

Additional iron preparations for the treatment of iron deficiency anaemia are known, such as iron-sucrose and iron-gluconate compounds. These compounds bind iron less tightly, resulting in a higher concentration of free $Fe^{3+}$ ions, which increases the toxicity of the iron compounds when administered parenterally and may lead to disturbance of digestion when administered orally.

An iron-containing preparation for parenteral injection should obviously satisfy several requirements including ready availability of the iron for haemoglobin synthesis, absence of local or general side-effects and stability on storage enabling a satisfactory shelf-life at ambient temperature.

In some cases, it is desirable to administer an iron preparation orally because this is most convenient for the recipients. A frequent disadvantage encountered after administration of iron preparations orally is impaired digestion. Good iron preparations should provide iron to the body in the gastro-intestinal tract in a controlled way in order to provide sufficient iron to be assimilated through the intestinal epithelium and should not have an adverse influence on the digestion as such.

Iron saccharide preparations for treatment of anaemia have been marketed for decades, and many variations in the manufacturing process and in the selection of starting materials have been suggested with a view to improving the stability of such preparations and to decrease the severity of side-effects encountered at their administration.

Results obtained in investigations, tests and practical experience indicate that the above-mentioned problems are related to the molecular weight distribution of the saccharides employed.

It is generally recognized that high molecular dextrans involve a greater risk of anaphylactic reactions than do low molecular weight dextrans, but is has also been found that the presence of carbohydrates of low molecular weight such as monosaccharides, resulting from an initial step of hydrolysis, may create difficulties as well. When reacted with iron by precipitating ferric hydroxide in a solution of a saccharide with an ample molecular weight distribution, the low molecular weight carbohydrates combine with iron to form complex or association compounds of their own. The latter compounds are less stable than the desired iron oligosaccharide compound of moderate molecular weight, causing precipitation of iron hydroxide or oxyhydroxide and/or gel-forming reactions possibly resulting in a complete solidification of the solution within days or months.

In view of the importance of the issue, considerable attention has been directed to the development of iron oligosaccharide compounds, wherein the oligosaccharide component presents an appropriate molecular weight distribution.

GB 1,076,219 discloses a method for the manufacture of a complex containing iron, low molecular weight dextrin or dextran and sorbitol for the prophylaxis or treatment of iron deficiency anaemia.

U.S. Pat. No. 4,927,756 describes a procedure for the manufacture of an iron dextran compound wherein the molecular weight of the dextrans is in the range of 2000-4000.

WO 1999/48533 discloses iron dextrans consisting of dextrans having a weight average molecular weight of 700 to 1400 and number average molecular weight of 400 to 1400 Daltons in stable association with ferric oxyhydroxide. The disclosed iron dextran complexes give rise to a reduced number of incidences of anaphylactic side effects.

WO 2003/087164 discloses iron dextrin compounds consisting of dextrins of a weight average molecular weight of 3,000 Daltons or less and a number average molecular weight of 400 Daltons or more in stable association with ferric oxyhydroxide. Said compounds show a low degree of toxicity.

In the light of the known methods and compounds mentioned in the above, however, there is still a need for further improving the stability of iron oligosaccharide compounds useable for the preparation of compositions for the treatment or prophylaxis of iron deficiency anaemia, so that they may be stored for an extended period at ambient temperature with no significant deterioration of their most important properties.

It is therefore an object of the present invention to provide an iron oligosaccharide compound with enhanced stability suitable for entering into compositions for the treatment or prophylaxis of iron deficiency anaemia. The compound should still fulfil the usual criteria within the art, which are: 1) high availability of iron for adsorption in the intestine without causing digestion problems when administered orally; 2) provision of iron in a form that is readily adsorbed in the intestine; 3) high availability of iron without risk of toxicity caused by high local concentration of $Fe^{3+}$ when administered parenterally; 4) minimum risk of anaphylactic reaction; 5) high iron content, and 6) ability to form solutions comprising a high amount of iron, which solutions fulfil the basal requirements for pharmaceutical compositions, i.e. being amenable to sterilization, preferably by autoclaving, and which are also stable during storage for a long period at ambient temperatures.

To meet this object, an iron oligosaccharide compound is provided according to the first aspect of the invention, which compound comprises a hydrogenated oligosaccharide in stable association with ferric oxyhydroxide, the hydrogenated oligosaccharide having a weight average molecular weight (Mw) of less than 3,000 Daltons, preferably approximately 1,000 Daltons, the content of dimer saccharide in said hydrogenated oligosaccharide being 2.9% by weight or less, based on the total weight of the hydrogenated oligosaccharide.

By way of example, the starting material for manufacturing of the hydrogenated oligosaccharide used in accordance with the invention may be Dextran 1, which satisfies the European Pharmacopoeia, entry 01/2009:1506. This starting material has according to the European Pharmacopoeia the following specifications: weight average molecular weight (Mw): 850 to 1150 Daltons, fraction with one or two saccharide (i.e. dimer) units: less than 15%, and fraction with more than 9 saccharide units: less than 20% by weight. Usually, the amount of dimer saccharide in Dextran 1 is around 8% by weight. By removing the smaller molecules by, e.g. membrane filtration, the desired amount of dimer saccharide of 2.9% by weight or less is obtained.

In the present context and in the following, the terms "weight average molecular weight" and "number average molecular weight" should be taken as the respective molecular weights of the oligosaccharide at the time where formation of complexes takes place, based on all oligosaccharide molecules from the monomer and upwards.

It has surprisingly been found that the amount of dimer in the oligosaccharide entering into stable association with iron(III)oxyhydroxide is a key factor with regard to the stability of the final compound, and that the effect is exerted in a highly non-linear manner. Usually, iron(III)-oxyhydroxid is the sole component used in the iron saccharide composition according to the invention. However, for certain applications, such as contrast agents having magnetic capabilities, it is desired to use a mixture of iron(II)-oxid and iron(III)-oxyhydroxid. The iron oligosaccharide compound of the invention includes compounds prepared from such mixture.

According to the invention, to present a satisfactory stability, the content of dimer must be brought down to or below 2.9% by weight. Thus, by controlling the amount of dimer in the oligosaccharide before reacting with iron, a stable iron oligosaccharide compound is provided in an effective and cost-efficient way. In the case of dextran or dextrin, which are both glucose polymers comprising α 1,6-bonds as well as α 1,4-bonds, the dimers in question are isomaltose (two glucose monomers joined by an α 1,6-bond) and maltose (two glucose monomers joined by an α 1,4-bond).

Preferably, the content of monomer saccharide in said hydrogenated oligosaccharide is 0.5% by weight or less, based on the total weight of the hydrogenated oligosaccharide. This serves to minimize the risk of toxic effects due to the release of free ferric ions from compounds of monomer and iron, especially when present in preparations for parenteral administration. In said preparations, an elevated concentration of free monomer saccharide, such as glucose, may also be undesirable per se.

According to one embodiment of the invention, the employed hydrogenated oligosaccharide is hydrogenated dextran having a weight average molecular weight (Mw) between 500 and 3000 Daltons, a number average molecular weight (Mn) above 500 Daltons, wherein 90% by weight of said dextran has molecular weights less than 3500 Daltons, and the Mw of the 10% by weight fraction of the dextran having the highest molecular weights is below 4500 Daltons. Preferably, the dextran has been subjected to membrane processes having a cut-off value of between 340 and 800 Daltons. In this way it is ensured that incidents of non-desired side-effects are minimized.

In an alternative embodiment, the hydrogenated oligosaccharide is hydrogenated dextrin having a number average molecular weight (Mn) higher than or equal to 500 Daltons, wherein the 10% fraction of said hydrogenated dextrin having the highest molecular weight has a weight average molecular weight (Mw) of less than 4500 Daltons, and 90% of the dextrins have a molecular weight of less than 3500 Daltons. Said dextrin has low toxicity and an appropriate viscosity that allows easy and reliable handling of solutions of the dextrin.

Suitably, the iron oligosaccharide compound according to the invention has an apparent molecular weight ($M_p$) of 120 to 180 kD. Preferably, the an apparent molecular weight ($M_p$) is between 130 and 160 kD.

It is implied that the apparent molecular weight is measured on an autoclaved aqueous solution prepared by dissolving in 1,000 water 400 g powder of hydrogenated oligosaccharide in stable solution with ferric oxyhydroxide, the amount of iron (Fe) of the powder being 25% by weight. Solutions comprising the compounds of the invention prepared by another method or in another concentration may result in an apparent molecular weight, which deviates from the present method.

The apparent molecular weight is measured using size exclusion chromatography. The columns are based on silica particles containing polar diol groups. The calibration is made using dextran and iron dextran as standards and 0.1% sodium azid as eluent.

The amount of iron in the iron oligosaccharide compound of the invention may vary in accordance to the intended use of the final composition. Generally, the amount of iron in the iron oligosaccharide compound is 50% by weight or less. Suitably, the amount of iron oligosaccharide is above 10% by weight.

In one embodiment, the content of dimer in the hydrogenated oligosaccharide is 2.5% by weight or less, alternatively 2.3% by weight or less.

Without wishing to be bound by any specific theory, it is assumed that the dimer in small amounts coordinates to the colloidal particle containing the complex between oligosaccharide and FeOOH. When the content of dimer exceeds 2.9%, the dimer apparently acts as "dissolver" of the colloidal particle, rendering the compound of oligosaccharide and FeOOH unstable and able to gelatinize over time.

In one embodiment of the invention, the iron oligosaccharide compound is sole or partial constituent of a dry powder that preferably has an iron content of 10-50% by weight. Alternatively, the iron oligosaccharide compound may be dissolved or dispersed in an aqueous liquid, preferably yielding an iron content in the resulting solution or dispersion of 1-30% w/v. When used as injection liquids, liquids comprising high amounts of iron offers the advantage that a smaller amount of the liquid needs to be injected in the subject being treated, which obviously is an advantage for the subject being treated as well for the person performing the treatment.

According to a further aspect of the invention, a composition is provided, said composition comprising a pharmacologically effective amount of a compound according to the first aspect of the invention, as well as at least one pharmaceutically acceptable carrier. The composition may be adopted for parenteral, oral or any other form of administration.

A pharmaceutical composition comprising an iron oligosaccharide compound according to the invention may be prepared using procedures that are well known by the skilled person. Examples of compositions for oral use are tablets, capsules, syrups, pastes and mixtures.

Pharmaceutical compositions comprising an iron oligosaccharide compound according to the invention may be formulated with additional nutritional or pharmaceutical agents, such as vitamins, preferably water-soluble vitamins, micronutrients such as trace metals, e.g. cobalt, copper, zinc or selenium, bacteriostatic agents, or antibiotics such as tylosin. Vitamins insoluble in water may even be emulsified into an aqueous solution comprising the iron oligosaccharide compound according to the invention by use of a suitable emulsifier.

According to yet an aspect of the invention, a process for preparing an iron oligosaccharide compound is provided, which process comprises the steps of:
  (a) hydrolysing a polysaccharide so as to reduce its molecular weight,
  (b) hydrogenating the resulting oligosaccharide to convert functional aldehyde groups into alcohol groups,
  (c) fractioning the hydrogenated oligosaccharide according to molecular weight, so that the purified fraction has a weight average molecular weight equal to or less than 3,000 Daltons,
  (d) combining the resultant fractionated hydrogenated oligosaccharide as an aqueous solution with at least one water-soluble ferric salt,
  (e) adding base to the resulting aqueous solution to form ferric hydroxide, and
  (f) heating the resultant basic solution to transform the ferric hydroxide into ferric oxyhydroxide in association with said oligosaccharide;
wherein step (c) comprises a procedure of purification by one or more membrane processes having a cut-off value between 340 and 800 Daltons, which procedure is continued until the content of dimer saccharide in the purified fraction of oligosaccharide has been reduced to 2.9 by weight or less, based on the total weight of the hydrogenated oligosaccharide. In principle, the purification could alternatively be done using other procedures for fractionation of oligosaccharides that are suitable for fractioning to a narrow range of molecular weights, e.g. chromatographic methods. However, purification by membrane processes is preferred. In any case, traditional fractionation technique based on precipitations is not a suitable fractionation technique for the present invention, as the oligosaccharide fraction obtained will be too diffuse.

Preferably, the initial hydrolysis of the polysaccharide is performed as an acid hydrolysis, using a strong mineral acid such as sulphuric acid, phosphoric acid or hydrochloric acid.

In a preferred embodiment, the hydrogenation of the resulting oligosaccharide is effected by addition of sodium borohydride in aqueous solution.

Preferentially, the obtained association of ferric oxyhydroxide with the oligosaccharide is stabilized by addition of at least one salt of an organic hydroxy acid, preferably selected from citrates.

Advantageously, said purification by one or more membrane processes having a cut-off value between 340 and 800 Daltons is continued until the content of monomer in the purified fraction of oligosaccharide has been reduced to 2.9% (w/w) or less.

The term polysaccharide is used in the present context to describe any polymer comprising monomer units of glucose. According to one embodiment, the applied polysaccharide is dextran.

The dextran is preferably purified in step (c) by one or more membrane processes having a cut-off value suitable for holding back dextran of molecular weight above 2,700 Daltons.

When adding base in step (e) to the resulting aqueous solution in order to form ferric hydroxide, said aqueous solution is preferably adjusted to a pH above 10.

The heating in step (f) favourably is carried out at a temperature above 100° C. until the solution turns into a black or dark brown colloidal solution, which after neutralisation is filtered, and one or more stabilizers are added. A useful filter is a 0.45 μm filter. Before addition of said stabilizers, the solution may also be subjected to further purification and stabilization using filtration, heating and membrane processes.

Finally, the resultant basic solution may in a preferred embodiment be dried to obtain the iron-dextran compound as a stable powder. Alternatively, the drying operation may be omitted, so that an injection liquid can be produced from the purified solution without intermediate drying thereof. The powder suitably contains an amount of iron (Fe) in the iron-dextran compound of 50% by weight or less.

According to an alternative embodiment, the polysaccharide employed is starch, or dextrin. Dextrins are usually made by depolymerisation of starch using known depolymerising means such as acids, bases or enzymes. Dependent on its origin, starch contains a certain amount of α 1,6-glucosidic bonds positioned at branch points of a polyglucose chain. Therefore, dextrins may also contain a similar low fraction of α 1,6-glucosidic bonds. By adjusting the conditions for the depolymerisation of the starch it may be possible to favour breakage of α 1,4-glucosidic bonds or α 1,6-glucosidic bonds, so that the ratio between these types of bonds differs between the original starch and the prepared dextrins.

One of the characteristic properties of starch and dextrin is their gelling properties. In contrast to dextran, starch and higher dextrins gels even at modest concentrations, which makes the handling more difficult.

The gelling tendencies of starch and dextrin are mitigated, when the molecular weight is reduced by hydrolysis. However, the hydrolysis should not be too extensive, as small dextrins, cf. above, may give rise to toxicity problems when combined with iron in an association complex. Preferably, starch is hydrolysed until it does not form strong coloured complexes with iodine. Solutions of starch hydrolysed to this extent comprise high amounts of dextrin in the desired molecular size range and present a viscosity that is sufficient low to allow easy and accurate handling. For hydrolysis of starch, hydrochloric acid is a preferred acid.

Before being combined with iron, the reducing capability of the dextrins is diminished. This may be done by hydrogenation of the terminal aldehyde groups of the dextrins to alcohols. This reduction may be performed using well known procedures. Hydrogenation using sodium borohydride is preferred. After the hydrogenation, the reducing capability of the dextrins should be less than 3.0% as determined by the cupric oxidation method.

In a preferred embodiment, dextrin in step (c) is purified to obtain a number average molecular weight (Mn) higher than or equal to 500 Daltons, wherein the 10% fraction of said hydrogenated dextrin having the highest molecular weight has a weight average molecular weight (Mw) of less than 4,500 Daltons, and 90% of the dextrins have a molecular weight of less than 3,500 Daltons.

In a particularly preferred embodiment the 10% fraction of the dextrins having the highest molecular weights has an average molecular weight less than 4,000 Da, 90% of the dextrins having molecular weights of less than 3,000 Daltons, and the 10% fraction having the lowest molecular weights has a weight average molecular weight of 800 Daltons or more. A dextrin of such a molecular weight distribution shows an appropriate viscosity and provides safe and stable association complexes with iron.

In step (d), the purified and hydrogenated dextrin as an aqueous solution is combined with at least one water-soluble ferric salt, a preferred example of which is ferrichloride.

In step (e), base is added to the resulting solution to form ferric hydroxide, preferably to obtain a pH above 8.5.

The resultant basic solution is heated in step (f) to transform the ferric hydroxide into ferric oxyhydroxide in association with the dextrin and preferably the heating is carried out at a temperature above 85° C. until the solution turns into a black or dark brown colloidal solution, which after neutralisation is filtered, and one or more stabilizers are added. Before addition of said stabilizers, the solution may also be subjected to further purification and stabilization using filtration, heating and membrane processes.

Finally, the resultant basic solution may in a preferred embodiment be dried to obtain the iron-dextrin compound as a stable powder. Alternatively, the drying operation may be omitted, so that an injection liquid can be produced from the purified solution without intermediate drying thereof.

According to a further aspect of the invention, the use of a compound according to the first aspect of the invention is provided for manufacture of a parenterally or orally administrable therapeutical composition for prophylaxis or treatment of iron-deficiency anaemia in animal or human subjects.

According to another aspect of the invention, a hydrogenated oligosaccharide is provided, having a weight average molecular weight (Mw) of less than 3,000 Daltons and a content of dimer saccharide of 2.9% by weight or less, and preferably a content of monomer of 0.5% by weight or less. Said oligosaccharide is an intermediate in the production of the iron oligosaccharide compound according to the first aspect of the invention.

According to an additional aspect of the invention, a process is provided for preparing said intermediate hydrogenated oligosaccharide according to the former aspect of the invention, which process comprises the steps of:
 (a) hydrolysing a polysaccharide so as to reduce its molecular weight,
 (b) hydrogenating the resulting oligosaccharide to convert functional aldehyde groups into alcohol groups, and
 (c) fractioning the hydrogenated oligosaccharide according to molecular weight, so that the purified fraction has a weight average molecular weight equal to or less than 3,000 Daltons,
wherein step (c) comprises a procedure of purification by one or more membrane processes having a cut-off value between 340 and 800 Daltons, which procedure is continued until the content of dimer saccharide in the purified fraction of oligosaccharide has been reduced to 2.9% by weight or less, based on the total weight of the hydrogenated oligosaccharide. Preferably, said purification is continued until the content of monomer in the purified fraction of oligosaccharide has been reduced to 0.5% by weight or less.

According to a further aspect of the invention, a process is provided for producing an injection liquid containing a compound according to the first aspect of the invention, in which process the iron oligosaccharide compound as a dry powder is dissolved in an aqueous medium, pH is adjusted, if necessary, optionally stabilizer is added, and the liquid is sterilized by filtration, before it is filled into ampoules or vials, or by autoclave treatment after filling into such ampoules or vials.

Alternatively, a liquid containing said compound is purified, adjusted as to iron content and pH, stabilized and sterilized by filtration before being filled into ampoules or vials or by autoclave treatment after being filled into said ampoules or vials.

The iron oligosaccharide compounds according to the invention are highly soluble in water, which makes it possible to prepare injection liquids containing a high amount of iron. According to one embodiment of the invention, an injection liquid adapted for administration in a human is provided, comprising 1-20% (w/v) iron. Another embodiment of the invention provides an injection liquid adapted for administration in an animal comprising 10-30% (w/v) iron.

Solutions of the iron oligosaccharide compounds according to the invention can be sterilized by autoclaving without substantial physical changes of the solutions. Thus, the solutions may be autoclaved without any significant change of the molecular weights of the complexes or the viscosity of the solution.

The aqueous solutions of the iron oligosaccharide compound may be preserved using any recognized preserving techniques such as autoclaving, filtration through a 0.2-0.5 micron filter under sterile conditions or addition of a preserving agent. As an example of a preserving agent 0.5% phenol can be mentioned.

However, autoclaving is a preferred method for preserving the aqueous solutions of the compound according to the invention. Particularly preferred is autoclaving at a temperature of 121-135° C. for a period of 5-40 minutes.

The aqueous solutions of the iron oligosaccharide compound according to the invention show excellent stability and are not liable to deterioration by storage such as by gellification or precipitation.

The invention will now be further illustrated by the following non-limiting examples.

BRIEF DESCRIPTION OF THE SEVERAL VIEWS OF THE DRAWING

FIG. 1 shows a plot of the $t_{1/2}$ vs. the dimer content of the iron oligosaccharide products.

EXAMPLES

Hydrolysis and Hydrogenation of Dextran
An amount of pre-hydrolysed dextran collected as permeate from a membrane having a cut-off value <5,000 Daltons is further hydrolysed at pH 1.5 at a temperature of 95° C.

The hydrolysis is monitored using gel permeation chromatography (GPC) and is terminated by cooling, when the molecular weight of the material being hydrolysed is estimated to have achieved the desired value, i.e. a weight average molecular weight of 700-1,400 Daltons.

In the hydrolysis, low molecular weight dextran is produced but also glucose and iso-maltose are formed. Upon hydrolysis, the disaccharide content is at 7-8% by weight.

After cooling and neutralization, the amount of monomer and dimer is reduced by membrane processes having a cut-off value of 340-800 Daltons. The concentration of monosaccharide and disaccharide in the solution is monitored by gel permeation chromatography, and fractionation goes on until a dimer concentration of 2.9% by weight or less and a monomer concentration of 0.5% by weight or less is achieved.

Thereafter, the content of dextran is determined by optical rotation and the amount of reducing sugar is determined by use of Somogyi's reagent. To bring down the reducing capability below 3%, sodium borohydride is added to the solution at basic pH. The applied ratio of sodium borohydride:fractionated dextran is 1:34.7.

The solution is neutralized to pH<7.0 and subsequently de-ionized. The average molecular weights and the molecular weight distribution are determined chromatographically. Chromatography reveals that the desired conditions, viz. that 90% by weight of the dextran has a molecular weight less than 2,700 Daltons and that the weight average molecular weight (Mw) of the 10% by weight fraction of the dextran having the highest molecular weight is below 3,200 Daltons, are fulfilled. The final yield of dextran after de-ionization is approximately 50% relative to the initial amount of pre-hydrolysed dextran.

Synthesis of Iron-Dextran 120 kg dextran as produced above is mixed as an 18% solution with 150 kg $FeCl_3$, 6 $H_2O$. To the agitated mixture, 93 kg $Na_2CO_3$ as a saturated aqueous solution is added, whereupon the pH is raised to 10.5 using 24 litres of concentrated aqueous NaOH (27% (w/v)).

The mixture thus obtained is heated above 100° C. until it turns into a black or dark brown colloidal solution. After cooling, the solution is neutralized using 12 litres concentrated hydrochloric acid to obtain a pH of 5.8. After filtration the solution is purified using membrane processes until the chloride content in the solution is less than 0.55% calculated on basis of a solution containing 5% (w/v) iron.

If the chloride content of the solution is less than desired to obtain an isotonic solution, sodium chloride is added and pH is finally adjusted to 5.6, and the solution is filtered through a 0.45 μm (or alternatively a 0.2 μm) membrane filter.

The solution is spray dried and the iron-dextran powder is ready for marketing or for further processing.

As an alternative to spray drying, the solution may be used for direct production of injection liquids having an iron content of e.g. 10% (w/v), as described above.

When using the iron-dextran powder for producing injection or infusion liquids, the powder is re-dissolved in an aqueous medium, the pH is checked and, if necessary, adjusted, and the solution is filled into ampoules or vials after being sterilized by filtration. Alternatively, the sterilization can take place by autoclaving after filling into ampoules or vials.

Analysis of the Stability of Iron Oligosaccharide Compounds Relative to their Content of Dimer A range of iron oligosaccharide compounds with differing contents of disaccharide were analysed with respect to their rate of hydrolysis and apparent molecular weight, both of which are indicative of the quality of the respective compounds.

The rate of hydrolysis of $Fe^{3+}$ from the compound of FeOOH and oligosaccharide in acidic solution (0.24 M HCl; 0.9% NaCl) is assumed to be correlated to the rate of physiological release of iron. Therefore, the rate of hydrolysis as expressed by the half-life ($t_{1/2}$) is an important parameter of the investigated compounds.

The hydrolysis of $Fe^{3+}$ was measured by optical absorbance at 2873 nm.

Besides, it was found that the thermostability of iron oligosaccharides is a function of their apparent molecular weight ($M_P$). Thus, such compounds are unstable to an unsatisfactory degree, if the apparent molecular weight markedly exceeds a value of 160,000 Daltons upon storage at an elevated temperature for three months as test solutions.

The results are shown in Table 1.

TABLE 1

| Iron oligosaccharide compound no. | Amount of dimer in oligosaccharide | $t_{1/2}$/hours | $M_P$/Daltons | Assessment after keeping at elevated temperature for 3 months |
|---|---|---|---|---|
| 1 | 0.5% | 25.5 | 133,490 | stable |
| 2 | 0.75% | 21.7 | 149,532 | stable |
| 3 | 0.75% | 22.5 | 146,353 | stable |
| 4 | 1.6% | 21.6 | 138,053 | stable |
| 6 | 1.6% | 18.3 | 145,250 | stable |
| 7 | 2.0% | 20.9 | 150,983 | stable |
| 8 | 2.0% | 20.3 | 142,664 | stable |
| 9 | 3.0% | 12.1 | 152,516 | unstable |
| 10 | 5.0% | 12.2 | 185,433 | unstable |
| 11 | 8.0% | 9.7 | 215,143 | unstable |

As appears from Table 1, the apparent molecular weight is in a desirable range, viz. about 130 kD to about 160 kD, when the amount of dimer in the oligosaccharide is less than 3%. The same holds true for the rate of hydrolysis as expressed by the half-life. The Half-life ($t_{1/2}$) is defined as the time at which the absorbance is the half of the value compared the absorbance at t=0.

The results shown in Table 1 above may be arranged into two series. When the results are plotted into a diagram of $t_{1/2}$ vs. the dimer content FIG. 1 appears. The two straight lines fitted into the two series show an interception at a dimer content of 3.5% by weight and $t_{1/2}$ of 12.6 hours.

The invention claimed is:

1. A process for preparing a mixture of hydrogenated dextran oligosaccharides, comprising:
   (a) hydrolysing a polysaccharide so as to reduce its molecular weight,
   (b) fractioning the oligosaccharide of (a) according to molecular weight, the fractioning including a procedure of purification, which procedure is continued until the content of dimer saccharide in the purified fraction of oligosaccharide has been reduced to 2.9% by weight or less, based on the total weight of the oligosaccharide, and
   hydrogenating the oligosaccharide resulting from step (a) or step (b)
   wherein said oligosaccharide produced in step (b) comprises a mixture of hydrogenated dextran oligosaccharides having the following molecular weight distribution:
   (i) a weight average molecular weight (Mw) between 500 and 3,000 Daltons, (ii) a number average molecular weight (Mn) above 500 Daltons;
(iii) 90% by weight of said hydrogenated dextran oligosaccharides have molecular weights of less than 3,500 Daltons, and
(iv) the Mw of the 10% by weight fraction containing the hydrogenated dextran oligosaccharides having the highest molecular weights is below 4,500 Daltons.

2. The process according to claim 1, wherein said purification is continued until the monomer saccharide content in the purified fraction of oligosaccharide has been reduced to 0.5% by weight or less, based on the total weight of the oligosaccharide.

3. A composition comprising a hydrogenated oligosaccharide obtained by the process according to claim 1 and further comprising at least one pharmaceutically acceptable carrier.

4. A hydrogenated oligosaccharide obtained by the process according to claim 2.

5. The process according to claim 1, wherein said procedure of purification is chromatography.

6. The process according to claim 1, wherein said procedure of purification is a membrane process.

7. The process according to claim 6, wherein said membrane process has a cut-off value of between 340 and 800 Daltons.

8. The process according to claim 1, which comprises hydrogenating the oligosaccharide resulting from step (a).

9. The process according to claim 1, which comprises hydrogenating the oligosaccharide resulting from step (b).

10. The process according to claim 1, further comprising sterilizing said mixture of hydrogenated dextran oligosaccharides by autoclaving.

11. The process according to claim 1, wherein the Mw of said mixture of hydrogenated dextran oligosaccharides is 1,600 Daltons or less.

12. The process according to claim 1, wherein the Mn of said mixture of hydrogenated dextran oligosaccharides is 1,600 Daltons or less.

13. The process according to claim 1, wherein 90% by weight of the hydrogenated dextran oligosaccharides in said mixture of hydrogenated dextran oligosaccharides have molecular weights of less than 2,700 Daltons.

14. The process according to claim 1, wherein the Mw of the 10% by weight fraction containing the hydrogenated dextran oligosaccharides having the highest molecular weights in said mixture of hydrogenated dextran oligosaccharides is below 3,200 Daltons.

15. The process according to claim 1, wherein said purification is continued until the monomer saccharide content in the purified fraction of oligosaccharide has been reduced to 2.5% by weight or less, based on the total weight of the oligosaccharide.

16. The process according to claim 1, wherein said purification is continued until the monomer saccharide content in the purified fraction of oligosaccharide has been reduced to 2.3% by weight or less, based on the total weight of the oligosaccharide.

17. A process for preparing a mixture of hydrogenated dextran oligosaccharides, comprising:
(a) hydrolysing a polysaccharide so as to reduce its molecular weight,
(b) fractioning the oligosaccharide of (a) according to molecular weight, the fractioning including a procedure of purification, which procedure is continued until the content of dimer saccharide in the purified fraction of oligosaccharide has been reduced to 2.3% by weight or less, based on the total weight of the oligosaccharide, and
hydrogenating the oligosaccharide resulting from step (a) or step (b),
wherein said oligosaccharide produced in step (b) comprises a mixture of hydrogenated dextran oligosaccharides having the following molecular weight distribution:
(i) a weight average molecular weight (Mw) between 500 and 1,600 Daltons,
(ii) a number average molecular weight (Mn) is above 500 Daltons,
(iii) 90% by weight of said hydrogenated dextran oligosaccharides have molecular weights of less than 2,700 Daltons,
(iv) the Mw of the 10% by weight fraction of the hydrogenated dextran oligosaccharides having the highest molecular weights is below 3,200 Daltons, and
(vi) the content of monomer saccharide in said hydrogenated oligosaccharide is 0.5% by weight or less, based on the total weight of the hydrogenated oligosaccharide.

18. The process according to claim 17, wherein said procedure of purification is chromatography.

19. The process according to claim 17, wherein said procedure of purification is a membrane process.

20. The process according to claim 19, wherein said membrane process has a cut-off value of between 340 and 800 Daltons.

21. The process according to claim 17, which comprises hydrogenating the oligosaccharide resulting from step (a).

22. The process according to claim 17, which comprises hydrogenating the oligosaccharide resulting from step (b).

23. The process according to claim 17, wherein the Mw of said oligosaccharide is approximately 1,000 Daltons.

24. The process according to claim 17, further comprising sterilizing said mixture of hydrogenated dextran oligosaccharides by autoclaving.

25. The process according to claim 17, wherein the Mw of said mixture of hydrogenated dextran oligosaccharides is 1,600 Daltons or less.

26. The process according to claim 17, wherein the Mn of said mixture of hydrogenated dextran oligosaccharides is 1,600 Daltons or less.

27. The process according to claim 17, wherein 90% by weight of the hydrogenated dextran oligosaccharides in said mixture of hydrogenated dextran oligosaccharides have molecular weights of less than 2,700 Daltons.

28. The process according to claim 17, wherein the Mw of the 10% by weight fraction containing the hydrogenated dextran oligosaccharides having the highest molecular weights in said mixture of hydrogenated dextran oligosaccharides is below 3,200 Daltons.

* * * * *